United States Patent [19]

Babin et al.

[11] Patent Number: 5,340,835

[45] Date of Patent: Aug. 23, 1994

[54] ESTERS OF 2,2-DIMETHYL-3-[(2,2-DIFLUORO-CYCLOPROPYLIDENE) METHYL]CYCLOPROPANE CARBOXYLIC ACIDS

[75] Inventors: Didier Babin, Montigny; Marc Benoit, Roquevaire; Jean-Pierre Demoute, Neuilly Plaisance; Fabienne Pilorge, Tournan en Brie; Nicole Reinier, Marseille, all of France

[73] Assignee: Roussel-UCLAF, France

[21] Appl. No.: 5,603

[22] Filed: Jan. 19, 1993

[30] Foreign Application Priority Data

Jan. 28, 1992 [FR] France ................. 92 00865

[51] Int. Cl.$^5$ .................... C07C 69/74; A01N 9/24
[52] U.S. Cl. .................. 514/531; 514/365; 514/427; 514/461; 514/521; 548/204; 548/562; 549/499; 558/407; 560/118; 562/500
[58] Field of Search .............. 560/118; 562/500; 548/201, 562; 549/499; 558/167; 514/531, 365, 427, 461, 521

[56] References Cited

FOREIGN PATENT DOCUMENTS 0003336 8/1979 European Pat. Off. .
0007255 1/1980 France .
2100263 12/1982 United Kingdom .

OTHER PUBLICATIONS

Euporean Search Report Rapport De Recherche No. 92 00865.

*Primary Examiner*—Robert Gerstl
*Attorney, Agent, or Firm*—Bierman and Muserlian

[57] ABSTRACT

A compound selected from the group consisting of all stereoisomeric forms and mixtures thereof of a compound of the formula

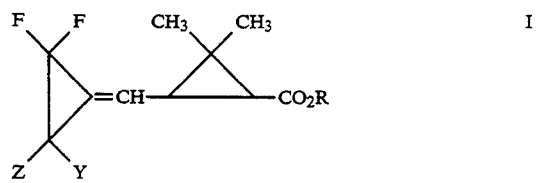

wherein Y and Z are individually selected from the groups consisting of hydrogen, halogen, —CF$_3$, alkyl, alkoxy and alkylthio of 1 to 8 carbon atoms and aryl, aryloxy and arylthio of up to 14 carbon atoms optionally substituted with at least one member of the group consisting of halogen, hydroxy optionally esterified etherified, —CF$_3$ and alkyl of 1 to 8 carbon atoms and R is alkyl of 1 to 8 carbon atoms or the remainder of a pyrethrinoid alcohol having excellent pesticidal properties and their preparation and intermediates.

20 Claims, No Drawings

ESTERS OF 2,2-DIMETHYL-3-[(2,2-DIFLUORO-CYCLO-PROPYLIDENE) METHYL]CYCLOPROPANE CARBOXYLIC ACIDS

OBJECTS OF THE INVENTION

It is an object of the invention to provide the novel compounds of formula I and a novel process and intermediates for their preparation.

It is another object of the invention to provide novel pesticidal compositions and a novel method of combatting pests.

These and other objects and advantages of the invention will become obvious from the following detailed description.

THE INVENTION

The novel esters of the invention are all stereoisomeric forms and mixtures thereof of a compound of the formula

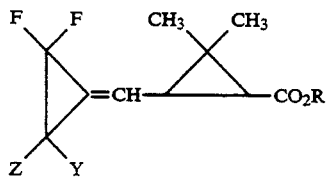

wherein Y and Z are individually selected from the groups consisting of hydrogen, halogen, —$CF_3$, alkyl, alkoxy and alkylthio of 1 to 8 carbon atoms and aryl, aryloxy and arylthio of up to 14 carbon atoms optionally substituted with at least one member of the group consisting of halogen, hydroxy optionally esterified or etherified, —$CF_3$ and alkyl of 1 to 8 carbon atoms and R is alkyl of 1 to 8 carbon atoms or the remainder of a pyrethrinoid alcohol.

The geometry of the double bond may be E or Z or a mixture of E and Z. The 2,2-dimethyl cyclopropane copula may have 1R cis or 1R trans structure or a mixture thereof. When Z is not hydrogen, the 2,2-difluorocyclopropane copula may have 1R cis or 1R trans structure or a mixture thereof.

Examples of alkyl are methyl, ethyl, n-propyl, isopropyl, n-butyl, isobutyl and tert-butyl and examples of cycloalkyl are cyclopropyl, cyclobutyl, cyclopentyl and cyclohexyl. Examples of alkenyl and alkynyl are vinyl, 1,1-dimethylallkyl, ethynyl and propynyl. An example of halogenated alkylidene is $CH_2$=CH—. Aryl is preferably phenyl or naphthyl. Examples of esterified or etherified hydroxy are —$OCH_3$, —$OCH_2CH_3$, —$OCH_2CH_2CH_3$, —$OCOCH_3$ and —$OCOC_6H_5$.

Among the preferred compounds of formula I are those wherein Y is hydrogen, those wherein Z is hydrogen, those wherein the double bond geometry is E and those wherein the 2,2-dimethyl-cyclopropane copula has 1R, cis structure.

Examples of R are a) alkyl of 1 to 8 carbon atoms, b) benzyl optionally substituted with at least one member of the group consisting of alkyl and alkoxy of 1 to 4 carbon atoms optionally substituted with at least one halogen, alkenyl and alkenyloxy of 2 to 6 carbon atoms, alkadienyl of 4 to 8 carbon atoms, methylenedioxy and halogen

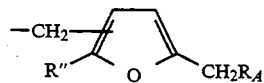

R" is hydrogen or methyl and $R_A$ is monocyclic aryl or —C≡CH,

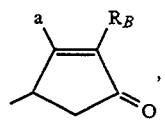

a is hydrogen or methyl and $R_B$ is an aliphatic of 2 to 6 carbon atoms and at least one unsaturation,

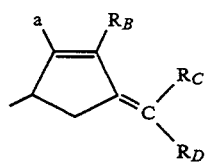

$R_C$ and $R_D$ are individually selected from the group consisting of hydrogen, halogen, alkyl or 1 to 6 carbon atoms, aryl or 6 to 10 carbon atoms, alkoxycarbonyl of 2 to 5 carbon atoms and 13 CN,

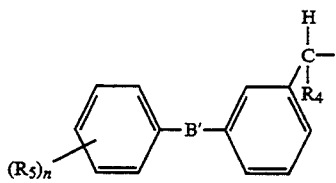

B' is selected from the group consisting of —O—, —S—,

—$CH_2$—, —SO— and —$SO_2$—, $R_4$ is selected from the group consisting of hydrogen, —CN, —$CH_3$, —$CONR_2$, —$CSNH_2$ and —C≡CH, $R_5$ is hydrogen or halogen or methyl and n is 0, 1, or 2,

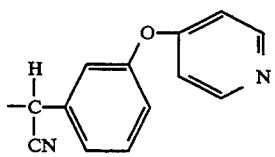

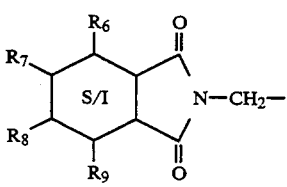

$R_6$, $R_7$, $R_8$ and $R_9$ are individually hydrogen or chlorine or methyl and S/I symbolizes an aromatic ring or a dihydro or tetrahydro ring i) 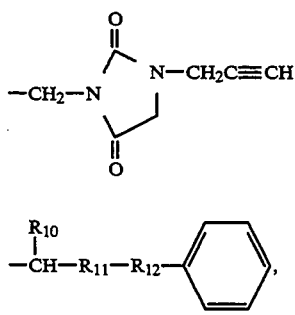

j) 

$R_{10}$ is hydrogen or —CN, $R_{12}$ is —CH$_2$— or —O—, $R_{11}$ is thiazolyl or thiadiazolyl bonded to

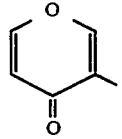

at any one of the possible positions and $R_{12}$ is bonded to $R_{11}$ through a carbon atom between the sulfur and nitrogen atoms, k) 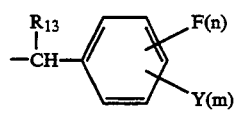

l) 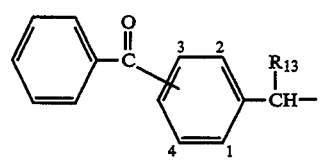

$R_{13}$ is selected from the group consisting of hydrogen, —CH$_3$, —CN and —C≡CH, n is an integer from 1 to 5, m is 5-n, Y are individually selected from the group consisting of hydrogen, halogen, —CH$_2$CN, —OH, optionally unsaturated alkyl optionally substituted with —CN, —COO alkyl, —CO alkyl, —(CH$_2$)$_m{'}$—O alkyl, '(CH$_2$)$_m{'}$—S alkyl, —(CH$_2$)$_m{'}$—N—(alkyl)$_2$ containing up to 12 alkyl carbon atoms and m' is 0, 1, 2, 3 or 4 and Si(alkyl)$_3$ the alkyl of up to 8 carbon atoms being optionally unsaturated, —O aryl and —(CH$_2$)$_m{'}$-aryl, the aryl containing up to 14 carbon atoms, m) 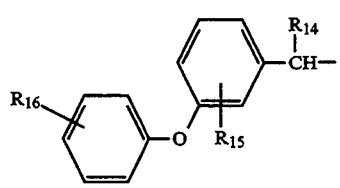

with the benzoyl being in the 3- or 4-position, n) 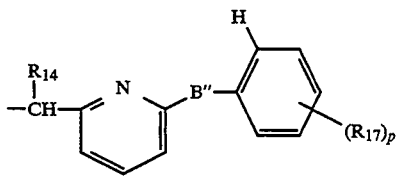

$R_{14}$ is selected from the group consisting of hydrogen, —CH$_3$, ethynyl and —CN, $R_{15}$ and $R_{16}$ are different and are hydrogen or fluorine or bromine, o) 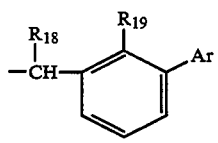

$R_{17}$ are individually selected from the group consisting of hydrogen, alkyl, alkoxy, alkylthio and alkyl sulfonyl of 1 to 4 carbon atoms, —CH$_3$, methylenedioxy, chloro, fluoro and bromo, p is 0, 1 or 2, B" is —O— or —S—,

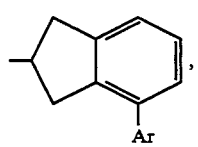

$R_{18}$ is selected from the group consisting of hydrogen, —CH$_3$, ethynyl and —CN, $R_{19}$ is different from $R_{18}$ and is hydrogen or fluorine or bromine, Ar is aryl of up to 14 carbon atoms, q) 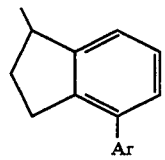

r) 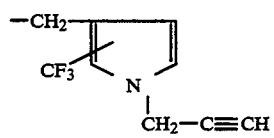

s) 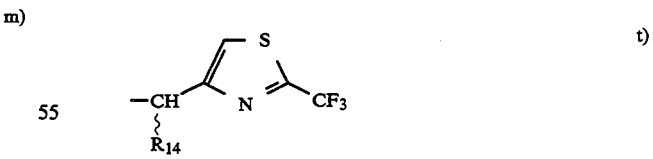

the —CF$_3$ being in any position of the pyrrolic ring, t) 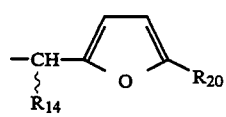

and u) 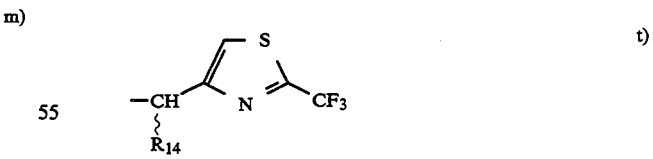

$R_{20}$ is alkyl of 1 to 4 carbon atoms optionally substituted with at least one halogen, $R_A$ is preferably 5-benzyl-3-furyl-methyl and $R_B$ is preferably —CH$_2$—CH=CH$_2$, —CH$_2$—CH=

CH—CH$_3$, —CH$_2$—CH=CH—CH$\alpha$CH$_2$, —CH$_2$—CH=CH—CH$_2$—CH$_3$, —CH$_2$—C≡CH, R$_5$ is preferably 3-phenoxy-benzyl, α-cyano -3-phenoxy-benzyl, α-ethynyl-3-phenoxy-benzyl, 3-benzoyl-benzyl, 1-(3-phenoxy-phenyl)-ethyl or α-thiamido-3-phenoxy-benzyl.

Among the preferred compounds of formula I are those where R is selected from the group consisting of

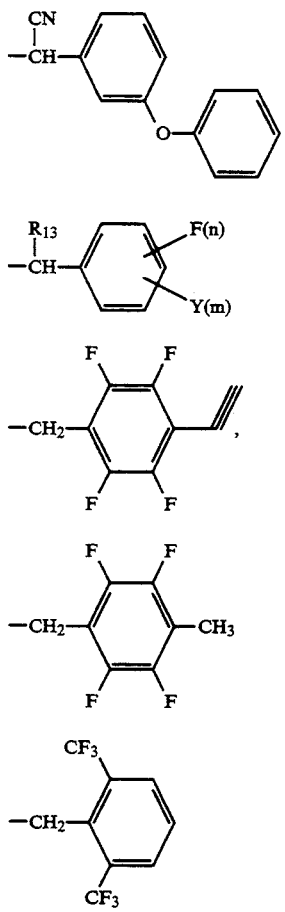

and n$_1$=3, 4 or 5,

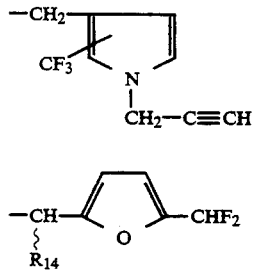

R$_{14}$ is hydrogen or ethynyl and

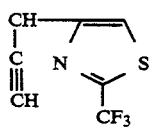

Among the preferred specific compounds of the invention are the compounds of Examples 2, 4, 6, 7, 8, 11, 12, 15, 16, 18 and 22.

The pesticidal compositions of the invention are comprised of a pesticidally effective amount of at least one compound of formula I and an inert carrier. The compositions may be in the form of powders, granules, suspensions, emulsions, solutions, aerosol solutions, combustible bands, baits or other known forms for these types of products.

The compositions generally contain a vehicle and/or a nonionic surface-active agent to ensure a uniform dispersion of the mixture. Examples of vehicles are liquids such as water, alcohol, hydrocarbons and other organic solvents, mineral, animal and vegetable oils, powders such as talc, clay, silicates and kieselghur or a combustible solid.

The compositions are useful for combatting parasites, for example for combatting parasites of premises, parasites of vegetation and parasites of warm-blooded animals. Thus, the compositions of the invention can be used for combatting insects, nematodes and parasitic acaridae of vegetation and animals particularly for combatting parasites of premises, parasites of vegetation and parasites of warm-blooded animals.

The compositions can be used to combat insects in premises, notably to combat flies, mosquitoes and cockroaches and can also be used to combat insects in the agricultural domain, to combat for example, aphides, the larvae of lepidoptera such as Drabrotica, as well as to combat insects of the soil. They are used at doses of 10 g to 300 g of active ingredient per hectare.

The products of formula I are in addition photostable and are not toxic to mammals. All of these properties make the compositions of the invention products which correspond perfectly to the demands of the modern agrochemical industry. They allow crops to be protected while preserving the environment.

The compositions can also be used to combat parasitic acaridae and nematodes of vegetation and can also be used to combat parasitic acaridae of animals, for example ticks and notably ticks of the Boophilus species, those of the Hyalomnia species, those of the Amblyomnia species, those of the Hyalomnia species or to combat all types of mites and notably the sarcoptic, psoroptic and chorioptic mite.

The insecticide compositions containing as active ingredient at least one of the products of formula I are particularly interesting.

The compositions are prepared according to the usual processes of the agrochemical industry or the veterinary industry or the industry for products intended for animal fodder. They may also contain additional pesticides.

The insecticide compositions of the invention preferably contain 0.005% to 10% by weight of active ingredient. According to an advantageous method for use in premises, the compositions according to the invention are used in the form of fumigant compositions. The compositions of the invention can then be advantageously constituted, for the non-active part, by a combustible insecticide coil, or also by an imcombustible fibrous substrate. In the latter case, the fumigant after incorporation of the active material is placed on a heating apparatus such as an electric vaporizer.

In the case where an insecticide Coil is used, the inert support can be, for example, pyrethrum marc compound, Tabu powder (or Machilus Thumbergii leaf powder), pyrethrum stem powder, cedar leaf powder, sawdust (such as pine sawdust), starch and coconut shell powder. The dose of active ingredient can then be 0.03% to 1% by weight. In the case where an incombustible fibrous support is used, the dose of active material can be 0.03% to 95% by weight.

The compositions of the invention for use in premises can also be obtained by preparing an oil based on the active ingredient, the oil impregnating the wick of a lamp and then being lit. The concentration of active ingredient incorporated in the oil is preferably 0.03 to 95% by weight.

The insecticide compositions of the invention, as well as the acaricide and nematocide compositions, can optionally have added to them one or more other pesticide agents. The acaricide and nematicide compositions can be in the form of powders, granules, suspensions, emulsions or solutions.

For acaricide use, wettable powders for foliar spraying containing 1 to 80%, or liquids for foliar spraying containing 1 to 500 g/liter of active ingredient are preferably used. Powders for foliar dusting can also be used containing 0.05 to 3% of active ingredient.

For nematocide use, liquids for soil treatment are preferably used containing 300 to 500 g/liter of active ingredient. The acaricide and nematocide compositions of the invention are preferably used at doses between 1 and 100 g of active ingredient per hectare.

To enhance the biological activity of the compositions of the invention, they can contain standard synergists used in such a case such as 1-(2,5,8-trioxadodecyl)-2-propyl-4,5-methylenedioxybenzene (or piperonyl butoxide) or N-(2-ethyl-heptyl)-bicyclo-[2,2-1]-5-heptene-2,3-dicarboximide, or piperonyl-bis-2-(2'-n-butoxyethoxy)ethylacetal (or tropital).

The novel method of the invention for combatting pests comprises contacting the pests with a pesticidally effective amount of at least one compound of formula I. Due to the fact that the compounds of formula I have an excellent general tolerance, the products of formula I are useful for combatting diseases caused by ticks and mites in man and in animals. The products of the invention may be used to combat lice in a preventive or curative way and to combat mites.

The products of formula I can be administered externally by spraying, by shampooing, by bathing or painting-on. The products for veterinary use can also be administered by painting the backbone by the so-called "pour-on" method. The products of the invention can also be used as biocides or as growth regulators.

The pesticidal compositions of the invention may also contain besides the compounds of formula I at least one second pesticidal ingredient selected from the group consisting of pyrethrinoid esters such as the esters of allethrolone, of 3,4,5,6-tetra-hydrophthalimidomethyl alcohol, of 5-benzyl-3-furyl methyl alcohol, of 3-phenoxybenzyl alcohol and of α-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropanecarboxylic acids, by the esters of 3phenoxybenzyl alcohol and of e-cyano-3-phenoxybenzyl alcohol with 2,2-dimethyl-3-(2,2-dichlorovinyl)-cyclopropanecarboxylic acids, by the esters of α-cyano-3-phenoxy-benzyl alcohol with 2,2-dimethyl-3-(2,2-dibromovinyl)-cyclopropane carboxylic acids, by the esters of 3-phenoxybenzyl alcohol with 2-para-chlorophenyl-2-isopropyl acetic acid, by the esters of allethrolone, of 3,4,5,6-tetrahydrophtalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane carboxylic acids, in which "halo" is fluorine, chlorine or bromine, it being understood that the compounds of formula I can exist in all their possible stereoisomer forms, as well as the acid and alcohol copulas of the above pyrethrinoid esters.

The process of the invention for the preparation of the compounds of formula I comprises reacting an acid of the formula

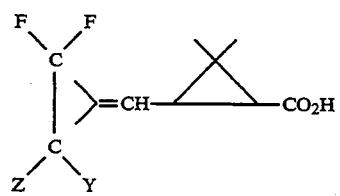

or a functional derivative thereof wherein Z and Y have the above definitions with an alcohol of the formula

R—OH  III or a functional derivative thereof wherein R has the above definition to obtain the corresponding compound of formula I. The esterification may be effected in the presence of a dehydration agent such as a tertiary base like pyridine. The esterification may also advantageously be effected in the presence of a mixture of dicyclohexylcarbodiimide and pyridine or 4-dimethylamino-pyridine.

The esterification may also be effected by reacting the acid chloride of the acid of formula II with the alcohol of formula III or with an organometallic derivative thereof or by transesterification of esters of the acid of formula II, preferably the acetate.

The compounds of formula III are generally known compounds and some of which are novel are described in the examples.

The compounds of formula II are novel and are an object of the invention. The compounds of formula II may be made by the following reaction scheme

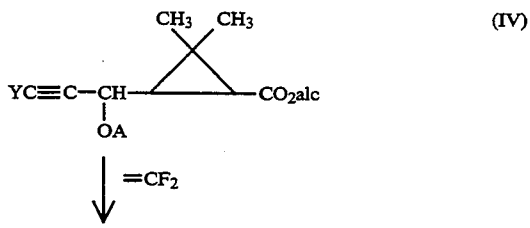

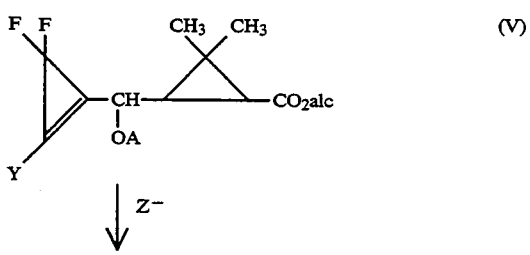

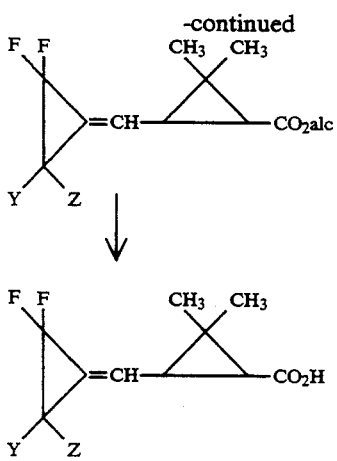

wherein A is acyl of a carboxylic acid of up to 8 carbon atoms optionally substituted by at least one halogen such as acetic acid or trifluoroacetic acid or acyl of a sulfonic acid such as mesylic acid or tosylic acid and alc is alkyl of 1 to 8 carbon atoms.

In a preferred mode of preparing the compounds of formula II, the compound of formula IV is reacted with a compound capable of generating a difluorocarbene "in situ" such as ClCF$_2$CO$_2$ Na, CF$_2$Br$_2$, CF$_2$ClH or CF$_2$Cl$_2$ to obtain a compound of formula V. The latter is reacted with an allylic transposition agent. To prepare the compounds of formula II where Z is hydrogen, the compound of formula VI is reacted with a reducing agent such as ($\phi_3$PCuH)$_6$ or $\phi_3$KBH or NaBH$_4$ in the presence of a catalyst. To prepare the compounds of formula II where Z is other than hydrogen, the reaction is effected with an allylic transposition agent to generate the Z$^-$ ion such as a generator of Hal$^-$, CF$_3^-$, alc$^-$, Oalc$^-$ or Salc$^-$.

The products of formula V are obtained in the form of a mixture of E and Z stereoisomers which can optionally be separated by chromatography.

The transformation of the ester of formula VI may be effected by classic procedures such as by reaction with trifluoroacetic acid. If desired, the mixture of E and Z acids may be separated by chromatography into the E acid and Z acid.

The compounds of formula IV are generally known compounds and can be prepared by the process of European patent No. 0105006, for example. 1,1-dimethylethyl [1R-(α, 3α(R)]-2,2-dimethyl-3-(1-acetoxypropynyl)-cyclopropane carboxylate is a novel product.

In the following examples, there are described several embodiments to illustrate the invention. However, it is to be understood that the invention is not intended to be limited to the specific embodiments.

EXAMPLE 1

2,3,5,6-tetrafluoro phenyl methyl [1R-[1alpha, 3alpha (Z)]] 2,2-dimethyl 3-[(2,2-difluorocyclopropylidene) methyl]cyclopropane carboxylate A solution containing 280 mg of dicyclohexyl-carbodiimide, 5.5 mg of 4-dimethylaminopyridine and 2 cm$^3$ of methylene chloride is introduced into a solution containing 275 mg of the Z isomer of the acid whose preparation is given hereafter (Preparation 1), 245 mg of 2,3,5,6-tetrafluoro-benzyl alcohol and 4 cm$^3$ of methylene chloride. Agitation is maintained for 6 hours, followed by filtering, rinsing with isopropyl ether and bringing to dryness. A product is obtained which is chromatographed on silica eluting with a hexane—isopropyl ether mixture (95-5). 240 mg of desired product is obtained. rf=0.15 (hexane—isopropyl ether 95-5).

EXAMPLE 2

(2,3,5,6-tetrafluoro phenyl) methyl [1R-[1alpha, 3alpha(E)]] 2,2-dimethyl 3-[(2,2-difluorocyclopropylidene) methyl]cyclopropane carboxylate By operating as in Example 1, starting with 420 mg of the E isomer of the acid obtained in Preparation 1 and 388 mg of 2,3,5,6-tetrafluoro benzyl alcohol, 360 mg of desired product is obtained. rf=0.15 (hexane—methylene chloride 8-2). M.p.=61.5° C.

EXAMPLE 3

(2,3,5,6-tetrafluoro 4-propynyl phenyl) methyl [1R-[1alpha, 3alpha(Z)]] 2,2-dimethyl 3-[(2,2difluorocyclopropylidene) methyl] cyclopropane carboxylate By operating as in Example 1, starting with 275 mg of the Z isomer of the acid obtained in Preparation 1 and 300 mg of 2,3,5,6-tetrafluoro 4-propynyl benzyl alcohol, 400 mg of desired product is obtained. M.p.=70.7° C.

EXAMPLE 4

(2,3,5,6-tetrafluoro 4-propynyl phenyl) methyl [1R-[1alpha, 3alpha(E)]] 2,2-dimethyl 3-[(2,2difluorocyclopropylidene) methyl] cyclopropane carboxylate By operating as in Example 1, starting with 420 mg of the E isomer of the acid obtained in Preparation 1 and 450 mg of 2,3,5,6-tetrafluoro 4-propynyl benzyl alcohol, 470 mg of desired product is obtained. rf=0.1 (hexane—methylene chloride 8-2).

EXAMPLE 5

[1- ( 2 -propynyl) 2-(trifluoro methyl) 1H-pyrrol 3-yl ]methyl [1R-[1alpha, 3alpha(E,Z)]] 2,2-dimethyl 3-[(2,2-difluorocyclopropylidene) methyl] cyclopropane carboxylate By operating as in Example 1, starting with 200 mg of the mixture of E, Z isomers of the acid obtained in Preparation 1 and 200 mg of [1-(2-propynyl) 2-(trifluoromethyl) 1H-pyrrol 3-yl] methyl alcohol, 240 mg of desired product is obtained. rf=0.10 (hexane—isopropyl ether 9-1).

EXAMPLE 6

1-cyano (3-phenoxyphenyl) methyl [1R-[1alpha(S), 3alpha(E,Z)]] 2,2-dimethyl 3-[(2,2-difluorocyclopropylidene) methyl]cyclopropane carboxylate By operating as in Example 1, starting with a mixture of E,Z isomers of the acid obtained in Preparation 1 and 1-cyano 3-phenoxy benzyl alcohol, the desired product is obtained. rf=0.08 (hexane—isopropyl ether 9-1).

By operating as in Example 1, the following desired products were obtained starting with the appropriate acid and alcohol.

EXAMPLE 7

(pentafluorophenyl) methyl [1R-[1alpha, 3alpha(E)]]2,2-dimethyl 3-[(2,2-difluorocyclopropylidene) methyl] cyclopropane carboxylate rf=0.2 (hexane—isopropyl ether 98-2)

EXAMPLE 8

(4-methyl 2,3,5,6-tetrafluorophenyl) methyl [1R-[1alpha, 3alpha(E)]] 2,2-dimethyl 3-[(2,2-difluorocyclo-propylidene) methyl]cyclopropane carboxylate rf=0.1 (hexane—isopropyl ether 98-2)

EXAMPLE 9

(2,6-difluorophenyl) methyl [1R-[1alpha, 3alpha (E)]]2,2-dimethyl 3-[(2,2-difluorocyclopropylidene) methyl] cyclopropane carboxylate rf=0.15 (pentane—methylene chloride 8-2)

EXAMPLE 10

(3-difluoromethoxyphenyl) methyl [1R-[1alpha, 3alpha(E)]] 2,2-dimethyl 3-[(2,2-difluorocyclopropylidene) methyl]cyclopropane carboxylate The 3-difluoromethoxy benzyl alcohol used at the start was prepared as indicated in the Patent DE 2831193A1. rf=0.3 (hexane—isopropyl ether 9-1)

EXAMPLE 11

(2,3,6-trifluorophenyl) methyl [1R-[1alpha, 3alpha(E)]]2,2-dimethyl 3-[(2,2-difluorocyclopropylidene) methyl] cyclopropane carboxylate rf=0.2 (hexane—isopropyl ether 9-1)

EXAMPLE 12

(2,6-bis trifluoromethylphenyl) methyl [1R- [1alpha, 3alpha (E) ]] 2,2-dimethyl 3-[(2,2-difluorocyclo-propylidene) methyl]cyclopropane carboxylate rf=0.18 (hexane—isopropyl ether 95-5)

EXAMPLE 13

(1-(3-phenoxypyridyl) ethyl [1R-[1alpha, 3alpha (E)]] 2,2-dimethyl 3-[(2,2-difluorocyclopropylidene) methyl] cyclopropane carboxylate rf=0.1 (hexane—isopropyl ether 9-1)

EXAMPLE 14

(1-cyano(2-fluoro 3-phenoxyphenyl) methyl [1R-[1alpha, 3alpha(E)]] 2,2-dimethyl 3-[(2,2-difluorocyclo-propylidene) methyl]cyclopropane carboxylate rf=0.09 (hexane—isopropyl ether 9-1)

EXAMPLE 15

(1-ethynyl (2-difluoromethylfuryl) methyl [1R-[1alpha, 3alpha(E)]] 2,2-dimethyl 3-[(2,2-difluorocyclo-propylidene) methyl]cyclopropane carboxylate rf=0.13 (hexane—isopropyl ether 9-1)

EXAMPLE 16

(2-fluoro 6-(trifluoromethyl) phenyl) methyl [1R-[1alpha, 3alpha(E)]] 2,2-dimethyl 3-[(2,2-difluorocyclo-propylidene) methyl] cyclopropane carboxylate rf=0.18 (hexane—isopropyl ether 95-5)

EXAMPLE 17

(2- (difluoromethyl) furyl) methyl [1R- [1alpha, 3alpha(E) ]] 2,2-dimethyl 3-[(2,2-difluorocyclopropylidene) methyl]cyclopropane carboxylate rf=0.15 (hexane—isopropyl ether 9-1)

EXAMPLE 18: (1-(2-trifluoromethyl thiazol-4-yl) 2-propynyl [1R-[1alpha, 3alpha(E)]] 2,2-dimethyl 3-[(2,2-difluorocyclo-propylidene) methyl] cyclopropane carboxylate rf=0.15 (hexane—methylene chloride 7-3)

EXAMPLE 19

(1-cyano (3-phenoxyphenyl) methyl [1R-[1alpha, 3alpha(Z)]] 2,2-dimethyl 3-[(2,2-difluoro 3(R or S)-n-butylcyclopropylidene) methyl] cyclopropane carboxylate rf=0.2 (hexane—isopropyl ether 9-1)

EXAMPLE 20

(2,3,5,6-tetrafluorophenyl) methyl [1R-[1alpha, 3alpha(Z)]] 2,2-dimethyl 3-[(2,2-difluoro 3(R or S)-n-butylcyclopropylidene) methyl] cyclopropane carboxylate rf=0.1 (hexane—methylene chloride 9-1)

EXAMPLE 21

(4-propynyl 2,3,5,6-tetrafluorophenyl ) methyl [1R-[1alpha, 3alpha(Z)]] 2,2-dimethyl 3-[(2,2-difluoro 3(R or S)-n-butylcyclopropylidene) methyl] cyclopropane carboxylate rf=0.12 (hexane—isopropyl ether 97-3)

EXAMPLE 22

(2,3,5,6-tetrafluorophenyl) methyl [1R-[1alpha, 3alpha(E)]] 2,2-dimethyl 3-[(2,2-difluoro 3-methylcyclo-propylidene) methyl] cyclopropane carboxylate rf=0.15 (hexane—methylene chloride 8-2)

EXAMPLE 23

(2,3,5,6-tetrafluorophenyl) methyl [1R-[1alpha, 3alpha(Z) ]] 2,2-dimethyl 3-[(2,2-difluoro 3-methylcyclopropylidene) methyl] cyclopropane carboxylate rf=0.1 (hexane—methylene chloride 9-1)

EXAMPLE 24

(4-propynyl 2,3,5,6-tetrafluorophenyl) methyl [1R-[1alpha, 3alpha(E) ]] 2,2-dimethyl 3-[(2,2-difluoro 3-methylcyclopropylidene) methyl] cyclopropane carboxylate rf=0.1 (hexane—isopropyl ether 97-3)

EXAMPLE 25

(4-propynyl 2,3,5,6-tetrafluorophenyl) methyl [1R-[1alpha, 3alpha(Z)]] 2,2-dimethyl 3-[(2,2-difluoro 3-methylcyclopropylidene) methyl] cyclopropane carboxylate rf=0.15 (hexane—isopropyl ether 95-5)

EXAMPLE 26

(1-cyano (3-phenoxyphenyl) methyl [1R- [1alpha, 3alpha(E)]] 2,2-dimethyl 3-[(2,2-difluoro 3-methylcyclo-propylidene) methyl] cyclopropane carboxylate rf=0.1 (hexane—isopropyl ether 9-1)

EXAMPLE 27

(1-cyano (3-phenoxyphenyl) methyl [1R-[1alpha, 3alpha(Z)]] 2,2-dimethyl 3-[(2,2-difluoro 3-methylcyclo-propylidene) methyl] cyclopropane carboxylate rf=0.15 (hexane—isopropyl ether 9-1)

EXAMPLE 28

1-(2-trifluoromethylthiazol-4-yl) 2-propynyl [1R-[1alpha, 3alpha(E)]] 2,2-dimethyl 3-[(2,2-difluoro 3-trifluoromethylcyclopropylidene) methyl] cyclopropane carboxylate rf=0.1 (hexane—isopropyl ether 95-5)

PREPARATION 1

[1R-[1alpha, 3alpha(Z)]] 2,2-dimethyl 3-[2,2-difluorocyclopropylidene] methyl cyclopropane carboxylic acid and corresponding E and Z isomers

STAGE A: (1,1-dimethyl) ethyl [1R-[1alpha, 3alpha(R)]] 2,2-dimethyl 3-[1-acetoxy propynyl) cyclopropane carboxylate.

10.8 cm$^3$ of acetic anhydride is introduced at 0° C. over 15 minutes into a solution containing 8.5 g of (1,1-dimethyl) ethyl [1R-[1alpha, 3alpha(R)]] 2,2-dimethyl 3-[1-hydroxy propynyl) cyclopropane carboxylate obtained as indicated in European Patent No. 0,105,006 and 25 cm$^3$ of pyridine. The reaction mixture is maintained under agitation for 6 hours, then it is poured into an aqueous solution of sodium acid phosphate, and extracted with isopropyl ether. After drying and bringing to dryness under reduced pressure, the product obtained is chromatographed on silica eluting with a hexane—isopropyl ether mixture (7-3). 9.44 g of product is obtained of rf=0.4. M.p.=67.2° C.

STAGE B: (1,1-dimethyl) ethyl [1R-[1alpha, 3alpha(R)]] 2,2-dimethyl 3-[1-acetoxy 1-(2,2-difluorocyclopropenyl) ethyl] cyclopropane carboxylate A solution containing 61.18 g of sodium chlorodi-fluoro-acetate and 230 cm$^3$ of diglyme is introduced at 160° C. over 2 hours and 45 minutes into a solution containing 10.7 g of the product obtained in Stage A, and 50 cm$^3$ of diglyme. The whole is kept under agitation for 1 hour, then cooled down to 20° C., poured into an aqueous solution of sodium acid phosphate and extracted with ether. After drying and bringing to dryness, the diglyme is eliminated, and the product is taken up with pentane, washed with water, dried and brought to dryness. The product is chromatographed on silica eluting with a hexane—isopropyl ether mixture (85-15). 8.57 g of desired product is obtained of rf=0.2.

STAGE C: (1,1-dimethyl) ethyl [1R-[1alpha, 3alpha(Z)]] 2,2-dimethyl 3-[2,2-difluorocyclopropylidene) methyl] cyclopropane carboxylate, corresponding E isomer, corresponding Z isomer.

26.6 g of copper triphenylphosphine hydride hexamer [o$_3$PCuH]$_6$ is added at ambient temperature to a solution containing 8.57 g of the product prepared in Stage B and 170 cm$^3$ of toluene. The reaction mixture is maintained under agitation for 1 hour. 80 cm$^3$ of pentane and 80 cm$^3$ of ethyl ether are added. Agitation takes place for 2 hours, clarcel is added and agitation takes place again, followed by filtering and bringing to dryness. The crude product obtained is chromatographed eluting with a hexane—methylene chloride mixture (95-5). After evaporation under reduced pressure, the following are obtained:

720 mg of E+Z mixture 2.83 g of Z isomer, rf=0.15 (hexane—methylene chloride 95-5)

2.97 g of E isomer, rf=0.1; M.p.=33.8° C.

STAGE D: [1R-[1alpha, 3alpha(Z)]] 2,2-dimethyl 3-[(2,2-difluorocyclopropylidene) methyl] cyclopropane carboxylic acid A solution containing 2.83 g the Z isomer product obtained in Stage C, 28 cm$^3$ of toluene and 180 mg of paratoluenesulphonic acid is taken to reflux for 1 hour 45 minutes. The reaction mixture is cooled down to 20° C., poured into ice-cooled water, extracted with isopropyl ether, dried and brought to dryness under reduced pressure. The product obtained is chromatographed eluting with a hexane—methylene chloride—acetone mixture (70-15-15). After evaporation under reduced pressure, 550 mg of desired product is collected. rf=0.15 (hexane—methylene chloride—acetone 70-15-15).

[1R-[1alpha, 3alpha(E)]] 2,2-dimethyl 3-[(2,2-difluorocyclopropylidene) methyl] cyclopropane carboxylic acid By operating as in the preparation of the Z acid starting with 2.97 g of the E starting ester, 1.88 g of desired product is obtained. rf=0.15 (hexane—methylene chloride—acetone 70-15-15) M.p.=78.9° C.

[1R-[1alpha, 3alpha(E+Z)]] 2,2-dimethyl 3-[(2,2-difluorocyclopropylidene) methyl] cyclopropane carboxylic acid By operating as in the preparation of the Z acid starting with 720 mg of the E+Z ester prepared previously, 320 mg of desired product is obtained. rf=0.15 (hexane—methylene chloride—acetone 70-15-15).

PREPARATION 2: [1R-[1alpha, 3alpha(E+Z)]] 2,2-dimethyl 3-[2,2-difluoro 3-methylcyclopropylidene] methyl cyclopropane carboxylic acid and corresponding E and Z isomers

STAGE A: (1,1-dimethyl) ethyl [1R-[1alpha, 3alpha(E+Z)]] 2,2-dimethyl 3-[1-hydroxy 1-[2,2-(difluorocyclopropenyl) ethyl]cyclopropane carboxylate.

20 g of the acetate obtained in Preparation 1B in 200 cm$^3$ of methanol is cooled down to 0°/+5° C., 63.5 cm$^3$ of a 1N aqueous soda solution is added over 45 minutes. Agitation takes place for 2 hours at 0°/+5° C., followed by pouring into an ice-cooled aqueous solution of sodium acid phosphate, extracting with ether, drying and evaporating the solvent. 17.24 g of expected product is obtained.

STAGE B: (1,1-dimethyl) ethyl [1R-[1alpha, 3alpha(E+Z)]] 2,2-dimethyl 3-[1-mesyloxy 1-[2,2-(difluorocyclopropenyl) ethyl]cyclopropane carboxylate.

4.95 cm³ of mesyl chloride is added to 16.9 g of the alcohol prepared in Stage A in solution in 100 cm³ of ether cooled down to 0°/+3° C. Agitation takes place then 8.95 cm³ of triethylamine in 35 cm³ of ether is added over 30 minutes. Agitation takes place for 2 hours at 0°/+3° C., followed by filtering, pouring into ice-cooled water, extracting with ether, washing with water, drying and evaporating the solvent. 20.18 g of expected product is collected.

STAGE C: (1,1-dimethyl) ethyl [1R-[1alpha, 3alpha(E+Z)]] 2,2-dimethyl 3-[2,2-difluoro 3(R or S)-methylcyclopropylidene-methyl]cyclopropane carboxylate 10 g of copper cyanide in 100 cm³ of tetrahydrofuran is cooled down to −20°/−25° C., 140 cm³ of a solution of methyllithium (1.6M) in ether is added, agitation takes place for 30 minutes at about −15° C., then the whole is poured into a solution cooled down to −30° C. containing 20.18 g of the mesylate obtained in Stage B in 200 cm³ of tetrahydrofuran. Agitation takes place for 30 minutes at −20° C., the whole is poured into an ice-cooled aqueous solution of ammonium chloride, followed by extraction with ether, washing with water, drying and evaporating the solvent. The residue is chromatographed on silica (eluant: hexane—methylene chloride 9-1) and 8.9 g of Z isomer product and 2.44 g of the corresponding E isomer are collected.

STAGE D: [1R-[1alpha, 3alpha(E+Z)]] 2,2-dimethyl 3-[2,2-difluoro 3-methylcyclopropylidene] methyl cyclopropane carboxylic acid and corresponding E and Z isomers.

4 g of the Z isomer obtained in Stage C in 40 cm³ of methylene chloride is cooled down to 0°/+2° C., 11 cm³ of trifluoroacetic acid is added and agitation takes place for 3 hours at 0°/+2° C. The reaction medium is poured into ice-cooled water, extracted with methylene chloride, washed with water, dried, the solvent is evaporated, the residue is chromatographed on silica (eluant: hexane - acetone - methylene chloride 70-15-15) and 2.11 g of expected product is collected in the form of the Z isomer. M.p.=53° C.

By operating in the same manner starting with 2.44 g of the E isomer ester obtained in Stage C, 1.31 g of expected product is obtained in the form of the E isomer.

M.p.=97.7° C.

PREPARATION 3: [1R-[1alpha, 3alpha(E+Z)]] 2,2-dimethyl 3-[2,2-difluoro 3-terbutylcyclopropylidene] methyl cyclopropane carboxylic acid and corresponding E and Z isomers The operation is carried out as in Preparation 2 by using at the start the acetate obtained in Stage B of Preparation 1 and terbutyllithium.

PREPARATION 4: [1R-[1alpha, 3alpha(E+Z)]] 2,2-dimethyl 3-[2,2-difluoro 3-trifluoromethylcyclopropylidene] methyl cyclopropane carboxylic acid and corresponding E and Z isomers STAGE A: (1,1-dimethyl) ethyl [1R-[1alpha, 3alpha(R)]] 2,2-dimethyl 3-(1-hydroxy 3-trifluoro 2-butynyl) cyclopropane carboxylate 1.75 cm³ of butyllithium (1,5M) is mixed with 5 cm³ of tetrahydrofuran at −40° C., gaseous trifluoro 1-propynyl (2.5M) is reacted, 500 mg of (1,1-dimethyl) ethyl 2,2-dimethyl 3-formyl cyclopropane carboxylate is added over 20 minutes at −60° C., followed by agitation for 30 minutes, pouring the reaction medium into a saturated aqueous solution of sodium acid phosphate, extracting with ether, drying, the solvent is evaporated off under reduced pressure, the residue is chromatographed on silica (eluant: hexane-ethyl acetate 9-1) and 400 mg of expected product is obtained. M.p.=45.7° C.

STAGE B: (1,1-dimethyl) ethyl [1R-[1alpha, 3alpha(R)]] 2,2-dimethyl 3-(1-acetoxy 3-trifluoro 2-butynyl) cyclopropane carboxylate The operation is carried out as in Stage A of Preparation 1 by using at the start 400 mg of the product obtained above and 0.48 cm³ of acetic anhydride. 410 mg of expected product is obtained.

STAGE C: (1,1-dimethyl) ethyl [1R-[1alpha, 3alpha(R)]] 2,2-dimethyl 3-[(1-acetoxy 1-(2 2-difluoro 3-trifluoromethyl cyclopropenyl) ethyl] cyclopropane carboxylate The operation is carried out as in Preparation 1 Stage B starting with 410 mg of the product obtained above in Stage B and 1.97 g of sodium chlorodifluoroacetate. 310 mg of expected product is obtained.

STAGE D: (1,1-dimethyl) ethyl [1R-[1alpha, 3alpha(E,Z)]] 2,2-dimethyl 3-[2 2-difluoro 3-trifluoromethylcyclopropylidene) methyl]cyclopropane carboxylate and its corresponding E and Z isomers 3.28 g of the product obtained in Stage C in 50 cm³ of hexane and 5 cm³ of tetrahydrofuran is cooled down to −60°/−70° C., 8.5 cm³ of tributyl potassium borohydride is added dropwise over 10 minutes. Agitation takes place for 10 minutes at −60° C., then the reaction medium is poured into an ice-cooled aqueous solution of potassium acid phosphate, followed by extracting with ether, drying and evaporating the solvent under reduced pressure and 4 g of expected product is obtained.

STAGE E: [1R-[1alpha, 3alpha(E+Z)]]2,2-dimethyl 3-[2,2-difluoro 3trifluoromethylcyclopropylidene[ methyl cyclopropane carboxylic acid and corresponding E and Z isomers The product obtained in the previous stage in 26 cm³ of methylene chloride is cooled down to −3° C., 6.6 cm³ of trifluoroacetic acid is added over 5 minutes, followed by agitation for 30 minutes at +10° C. then for 2 hours at 20° C. The reaction medium is poured into ice-cooled water, followed by extracting with methylene chloride, drying, evaporating the solvent. The residue is chromatographed on silica (eluant: hexane—ethyl acetate 1-1) and 1.8 g of expected product is obtained.

PREPARATION 5: 2,3,6-trifluoro benzyl alcohol 10.56 g of 2,3,6-trifluoro benzoic acid is dissolved at ambient temperature, under a nitrogen atmosphere, in 100 cm³ of tetrahydrofuran. The reaction medium is cooled down in an ice-methanol bath and a solution containing 10 cm³ of borane methyl sulphide complex at 10 millimoles/cm³ and 30 cm³ of tetrahydrofuran is added over 30 minutes. Agitation takes place again for 5 minutes and the temperature is allowed to return to ambient. The reaction medium is heated for 3 hours 30 minutes at 45°/50° C. The solution obtained is poured into an aqueous solution of sodium acid phosphate, followed by extracting with isopropyl ether, washing, drying and bringing to dryness. 10.6 g of a colourless liquid is obtained which is chromatographed on silica eluting with a hexane—ethyl acetate mixture (7-3). 8.8 g of desired product is obtained.

M.p.<50° C.

IR Spectrum (CHCl₃): OH: 3620 cm⁻¹ Aromatic: 1642, 1604, 1499 cm⁻¹

NMR Spectrum (CDCl₃, 60 Hz) ppm: Aromatic protons: 6.70–7.47; $\underline{CH_2}$—OH: 4.83; O$\underline{H}$: 2.20.

PREPARATION 6: 2,6-bis(trifluoromethyl) benzyl alcohol

STAGE A: methyl 2,6-bis(trifluoromethyl) benzoate

A solution containing 6 g of 2,6-bis (trifluoromethyl) benzoic acid, 60 ml of tetrahydrofuran and 11.58 ml of a 2N soda solution is agitated for 30 minutes at 20° C. The reaction medium is cooled down to 0° C. and 4.26 ml of dimethyl sulphate is added. Agitation takes place for 1 hour at 20° C. and another 2.1 ml of dimethyl sulphate is added and the reaction medium is maintained under agitation for 24 hours at 20° C. It is then poured into an aqueous solution of sodium bicarbonate, followed by extracting with isopropyl ether then with ethyl acetate, drying, filtering, rinsing and bringing to dryness. In this way, after chromatographing on silica (eluant hexane—ethyl acetate (9-1)) 5.59 g of desired product is obtained.

STAGE B: 2,6-bis(trifluoromethyl) benzyl alcohol 58 ml of a 1.2M solution of diisobutylaluminium hydride (DIBAH) is added at 0° C. to a solution containing 5.59 g of the product prepared in Stage A and 60 ml of toluene. The temperature is allowed to return to 20° C. and the reaction mixture is maintained under agitation for 4 hours. The medium is poured into a molar solution of potassium and sodium double tartrate. Extraction takes place with isopropyl ether, the aqueous phase is saturated with sodium chloride, followed by extracting with ethyl acetate, drying, filtering, rinsing and bringing to dryness. After chromatographing on silica (eluant: hexane—ethyl acetate (9-1)) 4.72 g of desired product is obtained.

PREPARATION 7: 5- (difluoromethyl) -2-furanmethanol

STAGE A: 5-(acetyloxy) methyl-2-furancarboxaldehyde 10.05 cm³ of acetyl chloride is added at 5° C. to a solution containing 16.2 g of 5-(hydroxy methyl) 2-furan-carboxaldehyde and 200 cm³ of methylene chloride. Then 11.4 cm³ of pyridine and 50 cm³ of methylene chloride are added. The reaction mixture is maintained under agitation for 3 hours at 20° C. It is then treated with an aqueous solution of sodium acid phosphate and extracted with methylene chloride, followed by drying and concentrating. After chromatography on silica eluting with a hexane—ethyl acetate mixture (7-3), 19.35 g of desired product is obtained.

STAGE B: 5- (difluoromethyl) -2-furan methanol acetate

A solution containing 7.26 cm³ of DAST (diethylamino sulphide trifluoride) and 30 cm³ of methylene chloride is added at 5° C. to a solution containing 10 g of the product prepared in Stage A and 100 cm³ of methylene chloride. The reaction mixture is agitated at 20° C. for half an hour and is taken to reflux for 1 hour. It is maintained under agitation for 18 hours at 20° C. and taken to reflux for 3 hours, then treated with sodium acid carbonate and extracted with methylene chloride. After drying and concentrating, 12 g of a product is obtained which is chromatographed on silica eluting with a hexane—ethyl acetate mixture (8-2). In this way 5.5 g of desired product is obtained.

STAGE C: 5-(difluoro methyl)-2-furanmethanol 34.8 cm³ of a normal soda solution is added to a solution containing 5.5 g of the product prepared in the preceeding stage and 100 cm³ of methanol. Agitation takes place for 1 hour at 20° C., followed by treating with a saturated solution of sodium acid phosphate. After concentration the product obtained is chromatographed on silica eluting with a hexane—ethyl acetate mixture 7-3. In this way 3.6 g of desired product is obtained.

PREPARATION 8: 5-(difluoromethyl) alpha-ethynyl 2-furan-methanol

STAGE A: 5-difluoromethyl 2-furancarboxaldehyde

A solution containing 6.5 cm³ of DMSO (dimethyl sulphoxide) and 60 cm³ of methylene chloride is added at −60° C. under a nitrogen atmosphere to a solution containing 3.84 cm³ of oxalyl chloride and 40 cm³ of methylene chloride. The reaction mixture is maintained under agitation at −60° C. and 3.6 g of 5-difluoromethyl 2-furanmethanol in solution in 30 cm³ of methylene chloride is added. Agitation takes place for 2 hours at −60° C. and a solution of 16.1 cm³ of triethylamine and 30 cm³ of methylene chloride is added over 15 minutes. The reaction mixture is maintained under agitation for half an hour at −60° C., then the temperature is allowed to rise to −20° C. and agitation is continued at this temperature for half an hour. It is poured into a solution of sodium acid phosphate, extracted with methylene chloride and dried. 3.6 g of product is obtained which is chromatographed on silica eluting with a hexane—ethyl-acetate mixture 8-2. After chromatography 2.5 g of desired product is obtained.

STAGE B: [5-difluoromethyl 2-furyl] 2-propynol 43 cm³ of a 0.5M solution of ethynyl magnesium bromide in tetrahydrofuran is added at 0° C. over one hour to a solution containing 2.5 g of the product prepared in Stage A and 30 cm³ of tetrahydrofuran. The reaction mixture is maintained under agitation at 0° C. for 1 hour. It is poured into a saturated aqueous solution of sodium acid phosphate. 3 g of product is obtained which is chromatographed on silica eluting with a hexane—ethyl acetate mixture (7-3). 2.5 g of desired product is obtained.

PREPARATION 9: alpha-ethynyl 2-(trifluoromethyl) 4-thiazolyl methanol 11 cm³ of a molar solution of ethynyl magnesium bromide is added to a solution of tetrahydrofuran containing 2 g of 2-(trifluoromethyl) 4-thiazolecarboxaldehyde. The reaction mixture is maintained under agitation for 30 minutes at about 20° to 25° C. It is poured into a solution of ammonium chloride, followed by extraction with methylene chloride, drying, filtering and bringing to dryness. 2.1 g of desired product is obtained.

EXAMPLE 29

Preparation of a Soluble Concentrate

A homogeneous mixture is produced of the following:

| | |
|---|---|
| Product of Example 2 | 0.25 g |
| Piperonyl butoxide | 1.00 g |
| Tween 80 | 0.25 g |
| Topanol A | 0.1 g |
| Water | 98.4 g |

EXAMPLE 30

Preparation of an Emulsifiable Concentrate

The following are intimately mixed together:

| | |
|---|---|
| Product of Example 4 | 0.015 g |
| Piperonyl butoxide | 0.5 g |
| Topanol A | 0.1 g |
| Tween 80 | 3.5 g |
| Xylene | 95.885 g |

EXAMPLE 31

Preparation of an Emulsifiable Concentrate

A homogeneous mixture is produced of the following:

| | |
|---|---|
| Product of Example 2 | 1.5 g |
| Tween 80 | 20.00 g |
| Topanol A | 0.1 g |
| Xylene | 78.4 g |

EXAMPLE 32

Preparation of a Fumigant Composition

The following are mixed together in a homogeneous manner:

| | |
|---|---|
| Product of Example 4 | 0.25 g |
| Tabu powder | 25.00 g |
| Cedar leaf powder | 40.00 g |
| Pine sawdust | 33.75 g |
| Brilliant green | 0.5 g |
| p-Nitrophenol | 0.5 g |

BIOLOGICAL STUDY

A) Study of the Lethal Effect on *Spodotera littoralis* larvae

The tests were carried out by topical application of an acetone solution on the dorsal thorax of the larvae, using an Arnold micro-manipulator. 15 larvar are used per dose of the product to be tested. The larvar used are fourth-stage larvae, that is to say aged about 10 days having been reared at 24° C. and 65% relative humidity. After treatment, the individuals are placed on an artificial nutritive medium (Poitout medium).

The mortality check is carried out 48 hours after treatment.

At a dose of 10 ppm the products of Examples 6, 13, 14 and 27 have a good activity.

B) Study of the Activity on Diabrotica

The test insects are final stage larvae of Diabrotica. A 9 cm diameter disc of filter paper, placed at the bottom of Petri dish, is treated using 2 cm³ of an acetone solution. After drying 10 larvae per dose are deposited and the mortality check is carried out 24 hours after treatment.

At a dose of 10 ppm the products of Examples 2, 4, 7, 8, 11, 12, 15, 16, 18 and 22 have a good activity.

C) Study of the Lethal Effect on *Aphis cracivora*

7-day old adults are used and 10 Aphis are employed per concentration used. A contact-ingestion method is used. The treatment is carried out using a Fisher gun on a bean leaf which is deposited in a plastic Petri dish on a damp paper disk. The treatment is carried out using 2 cm³ of an acetonic solution of the product to be tested (1 cm³ per leaf side). The infestation by the insects is carried out after drying the leaf. The insects are kept in contact with the leaf for one hour. The insects are placed on non-treated leaves and a mortality check is carried out at the end of 24 hours.

Results

At a dose of 10 ppm the products of Examples 3, 4, 6, 8, 13, 14, 19, 21, 24, 25, 26 and 27 have a good activity.

What we claim is:

1. A compound selected from the group consisting of all stereoisomeric forms and mixtures thereof of a compound of the formula

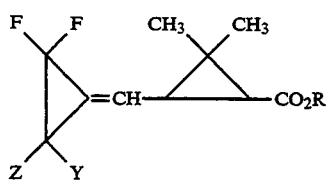

wherein Y and Z are individually selected from the group consisting of hydrogen, halogen, —CF₃, alkyl, alkoxy and alkylthio of 1 to 8 carbon atoms and hydrocarbyl aryl, aryloxy and arylthio of up to 14 14 carbon atoms optionally substituted with at least one member of the group consisting of halogen, hydroxy, optionally esterified or etherified, —CF₃ and alkyl of 1 to 8 carbon atoms and R is selected from the group consisting of a) alyl of 1 to 8 carbon atoms, b) benzyl optionally substituted with at least one member of the group consisting of alkyl and alkoxy of 1 to 4 carbon atoms optionally substituted with at least one halogen, alkenyl and alkenyloxy of 2 to 6 carbon atoms, alkadienyl of 4 to 8 carbon atoms, methylenedioxy and halogen

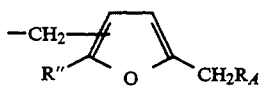                                                 c)

R'' is hydrogen or methyl and $R_A$ is monocyclic aryl or —C≡CH,

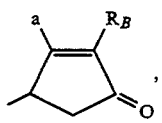                                                 d)

a is hydrogen or methyl and $R_B$ is an aliphatic of 2 to 6 carbon atoms with at least one unsaturation,

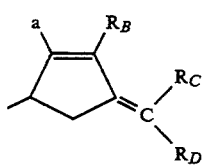                                                 e)

$R_C$ and $R_D$ are individually selected from the group consisting of hydrogen, halogen, alkyl of 1 to 6 carbon atoms, aryl of 6 to 10 carbon atoms, alkoxycarbonyl of 2 to 5 carbon atoms and —CN,

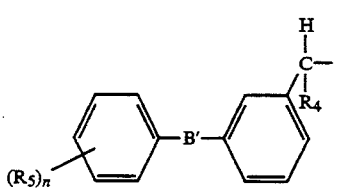

B' is selected from the group consisting of —O—, —S—,

—CH₂—, —SO— and —SO₂—, $R_4$ is selected from the group consisting of hydrogen, —CN, —CH₃, —CONH₂, CSNH₂ and —C≡CH, $R_5$ is hydrogen or halogen or methyl and n is 0, 1 or 2,

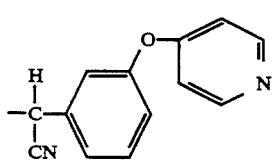                                                 g)

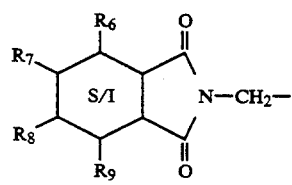                                                 h)

$R_6$, $R_7$, $R_8$ and $R_9$ are individually hydrogen or chlorine or methyl and S/I symbolizes an aromatic ring of a dihydro or tetrahydro ring

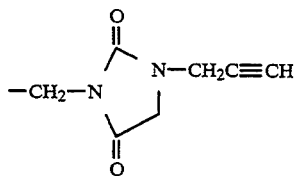                                                 i)

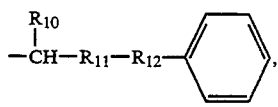                                                 j)

$R_{10}$ is hydrogen or —CN, $R_{12}$ is —CH₂— or —O—, $R_{11}$ is thiazolyl or thiadiazolyl bonded to $$\underset{\underset{\text{CH}}{|}}{\overset{\overset{R_{10}}{|}}{-}}-$$

at any one of the possible positions and $R_{12}$ is bonded to $R_{11}$ through a carbon atom between the sulfur and nitrogen atoms,

                                                k)

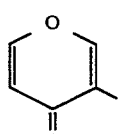                                                l)

$R_{13}$ is selected from the group consisting of hydrogen, —CH₃, —CN and —C≡CH, n is an integer from 1 to 5, m is 5-n, Y are individually selected from the group consisting of hydrogen, halogen, —CH₂CN, —OH, optionally unsaturated alkyl optionally substituted with —CN, —COO alkyl, —CO alkyl, —(CH₂)m'—O alkyl, —(CH₂)m'-S alkyl, —(CH₂)m'-N-(alkyl)₂ containing up to 12 alkyl carbon atoms and m' is 0, 1, 2, 3 or 4 and Si(alkyl)₃ the alkyl of up to 8 carbon atoms being optionally unsaturated, —O aryl and —(CH₂)m'-aryl, the aryl containing up to 14 carbon atoms,

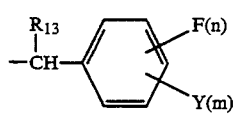                                                m)

with the benzoyl being in the 3- or 4-position,

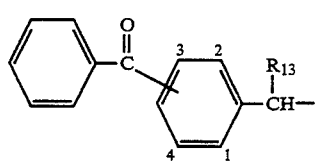                                                n)

$R_{14}$ is selected from the group consisting of hydrogen, —$CH_3$, ethynyl and —CN, $R_{15}$ and $R_{16}$ are different and are hydrogen or fluorine or bromine, o)
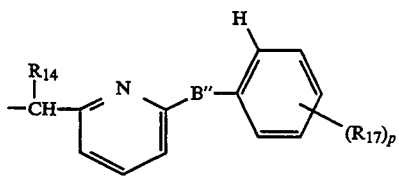

$R_{17}$ are individually selected from the group consisting of hydrogen, alkyl, alkoxy, alkylthio and alkyl sulfonyl of 1 to 4 carbon atoms, —$CF_3$, methylenedioxy, chloro, fluoro and bromo, p is 0, 1 or 2, B″ is —O— or —S—, p)
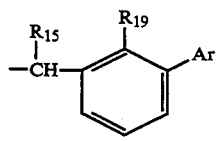

$R_{18}$ is selected from the group consisting of hydrogen, —$CH_3$, ethynyl and —CN, $R_{19}$ is different from $R_{18}$ and is hydrogen or fluorine or bromine, Ar is aryl of up to 14 carbon atoms, q)
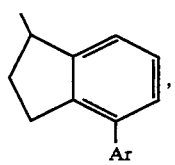

r)
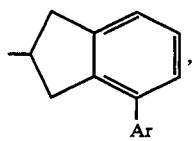

s)
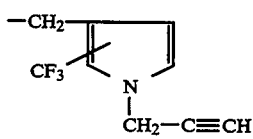

the —$CF_3$ being in any position of the pyrrolic ring t)
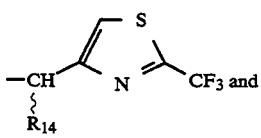

u)
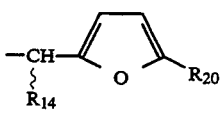

$R_{20}$ is alkyl of 1 to 4 carbon atoms optionally substituted with at least one halogen.

2. A compound of claim 1 wherein Y is hydrogen.
3. A compound of claim 1 wherein Y and Z are hydrogen.
4. A compound of claim 1 wherein the 2,2-dimethylcyclopropane coupla has 1R, cis structure.
5. A compound of claim 1 wherein the geometry of the double bond is E.
6. A compound of claim 1 wherein R is

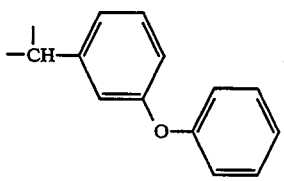

7. A compound of claim 1 wherein R is

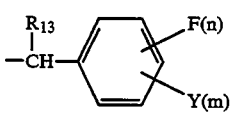

wherein $R_{13}$, m, n and y have the definitions of claim 1.
8. A compound of claim 1 wherein R is

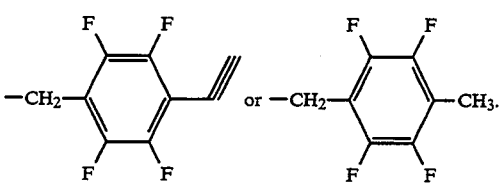

9. A compound of claim 1 wherein R is

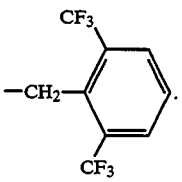

10. A compound of claim 1 wherein R is

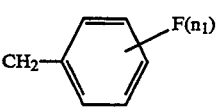

and n is 3 or 4 or 5.
11. A compound of claim 1 wherein R is

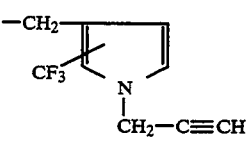

12. A compound of claim 1 wherein R is

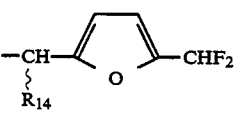

and $R_{14}$ is hydrogen or ethynyl.

13. A compound of claim 6 wherein R is

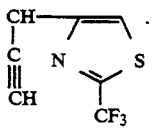

14. A compound of claim 1 selected from the group consisting of 2,3,5,6-tetrafluorobenzyl, 1R-[1α, 3α(E)]] 2,2-dimethyl 3-[2,2-difluorocyclopropylidene) methyl] cyclopropane carboxylate, 2,3,5,6-tetrafluoro-4-propynyl benzyl, 1R-[1α, 3α(E)]]2,2-dimethyl 3-[(2,2-difluorocyclopropylidene) methyl] cyclopropane carboxylate, (1-cyano 3-phenoxy-benzyl) [1R-[1α(S), 3α(E,Z)]] 2,2-dimethyl 3-[(2,2- difluorocyclopropylidene) methyl] cyclopropane carboxylate, 4-methyl 2,3,5,6-tetrafluoro-benzyl, 1R-[1α, 3α(E,Z)]2,2-dimethyl 3-[2,2-difluorocyclopropylidene) methyl] cyclopropane carboxylate, pentafluorobenzyl [1R-[1α, 3α(E)]] 2,2-dimethyl 3-[(2,2-difluorocyclopropylidene) methyl] cyclopropane carboxylate, 2,3,6 trifluorobenzyl [1R-[1α, 3α(E)]] 2,2-dimethyl 3-[(2,2-difluorocyclopropylidene) methyl] cyclopropane carboxylate, 2,6-bis trifluoromethyl-benzyl [1R-[1α, 3α(E)]] 2,2-dimethyl 3-[(2,2-difluorocyclopropylidene) methyl] cyclopropane carboxylate, 1-ethynyl-2-(difluoromethyl)furyl methyl [1R-[1α, 3α(E)]] 2,2-dimethyl 3-[(2,2-difluorocyclopropylidene) methyl] cyclopropane carboxylate, 2-fluoro 6-trifluoromethyl-benzyl [1R-[1α, 3α(E)]] 2,2-dimethyl 3-[(2,2-difluorocyclopropylidene) methyl] cyclopropane carboxylate, 1-(2-trifluoromethyl thiazol-4-yl)-2-propynyl [1R-[1α, 3α(E)]] 2,2-dimethyl 3-[(2,2-difluorocyclopropylidene) methyl] cyclopropane carboxylate and (2,3,5,6-tetrafluoro-benzyl) [1R-[1α, 3α(E)]] 2,2-dimethyl 3-[(2,2-difluoro 3-methylcyclopropylidene) methyl] cyclopropane carboxylate.

15. An insecticidal composition comprising an insecticidally effective amount of at least one compound of claim 1 and an inert carrier.

16. An insecticidal composition of claim 15 also containing at least one member of the group consisting of esters of allethrolone, of 3,4,5,6-tetrahydrophthalimidomethyl alcohol, of 5-benzyl-3-furyl methyl alcohol, of 3-phenoxybenzyl alcohol and of α-cyano-3-phenoxy-benzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropane carboxylic acid, by the esters of 3-phenoxybenzyl alcohol and of α-cyano-3-phenoxybenzyl alcohol with 2,2-dimethyl-3-(2,2-dichlorovinyl)-cyclopropane carboxylic acid, by the esters of α-cyano-3-phenoxybenzyl alcohol with 2,2-dimethyl-3-(2,2-dibromovinyl)-cyclopropane carboxylic acid, by the esters of 3-phenoxybenzyl alcohol with 2-parachlorophenyl-2-isopropyl acetic acid, by the esters of allethrolone, of 3,4,5,6,-tetrahydrophtalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane carboxylic acids, in which "halo" is fluorine, chlorine or bromine.

17. A method of combatting insects comprising contacting insects with an insecticidally effective amount of at least one compound of claim 1.

18. A compound of the formula

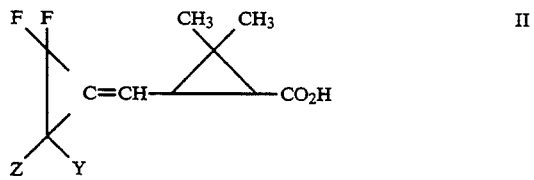

wherein Y and Z have the definition of claim 1.

19. A compound of claim 19 wherein Y and Z are hydrogen.

20. A compound selected from the group consisting of the E isomer, Z isomer and mixtures of E and Z isomers of 1,1-dimethyl-ethyl 1R-[1α, 3α] 2,2-dimethyl -3- [2,2-difluorocyclopropylidene) —cyclopropane carboxylate.

* * * * *